(12) United States Patent
Purcell

(10) Patent No.: US 10,111,903 B2
(45) Date of Patent: Oct. 30, 2018

(54) DELIVERY VEHICLE FOR THERAPEUTIC GASES

(71) Applicant: TECHNOLOGIES KHLÔROS INC., Quebec (CA)

(72) Inventor: Marc Purcell, Quebec (CA)

(73) Assignee: TECHNOLOGIES KHLÔROS INC., Québec, QC (CA)

( * ) Notice: Subject to any disclaimer, the term of this patent is extended or adjusted under 35 U.S.C. 154(b) by 0 days.

(21) Appl. No.: 15/710,408

(22) Filed: Sep. 20, 2017

(65) Prior Publication Data

US 2018/0008631 A1 Jan. 11, 2018

Related U.S. Application Data

(63) Continuation of application No. 15/504,832, filed as application No. PCT/CA2015/050786 on Aug. 19, 2015, now abandoned.

(60) Provisional application No. 62/040,195, filed on Aug. 21, 2014.

(51) Int. Cl.
*A61K 33/00* (2006.01)
*A61K 9/50* (2006.01)
*A61K 9/00* (2006.01)

(52) U.S. Cl.
CPC ............... *A61K 33/00* (2013.01); *A61K 9/006* (2013.01); *A61K 9/5015* (2013.01)

(58) Field of Classification Search
None
See application file for complete search history.

(56) References Cited

U.S. PATENT DOCUMENTS

| | | | |
|---|---|---|---|
| 3,012,893 A | 12/1961 | Kremzner et al. | |
| 3,985,909 A | 10/1976 | Kirkpatrick | |
| 3,985,910 A | 10/1976 | Kirkpatrick | |
| 4,001,457 A | 1/1977 | Hegadorn | |
| 4,289,794 A * | 9/1981 | Kleiner | A23G 3/52 426/474 |
| 7,887,832 B2 * | 2/2011 | First | A61K 9/0095 424/440 |
| 2003/0235613 A1 | 12/2003 | First et al. | |
| 2005/0089567 A1 | 4/2005 | First et al. | |

FOREIGN PATENT DOCUMENTS

| | | |
|---|---|---|
| IL | 165843 | 12/2010 |
| IL | 165843 A | 12/2010 |
| WO | 02/062152 A1 | 8/2002 |

* cited by examiner

*Primary Examiner* — Robert A Wax
*Assistant Examiner* — Melissa S Mercier
(74) *Attorney, Agent, or Firm* — Norton Rose Fulbright LLP

(57) ABSTRACT

The present invention relates to a buccal delivery dosage form and its use for administration of a therapeutic gas for buccal mucosal absorption of the therapeutic gas in the mouth of a subject. The buccal delivery dosage form comprises at least one crystallized excipient and at least one therapeutic gas entrapped within the crystallized excipient.

11 Claims, 2 Drawing Sheets

DELIVERY VEHICLE FOR THERAPEUTIC GASES

CROSS-REFERENCE TO RELATED APPLICATIONS

This application is a continuation application of U.S. Ser. No. 15/504,832 filed Feb. 17, 2017, still pending, which is a national stage entry of PCT application PCT/CA2015/050786 filed Aug. 19, 2015, which claimed priority from provisional application U.S. Ser. No. 62/040,195 filed Aug. 21, 2014, the entire content is these applications being incorporated in their entirety.

TECHNOLOGICAL FIELD

The present invention generally relates to a therapeutic gas-containing crystal for use as a vehicle for absorption or uptake of the therapeutic gas through the buccal mucosa.

BACKGROUND ART

Sublingual and buccal medications are administered by placing them in the mouth, either under the tongue (sublingual) or between the gum and the cheek (buccal). The medications dissolve rapidly and are absorbed through the mucous membranes of the mouth, where they enter into the bloodstream. Within the oral mucosal cavity, the buccal, including sublingual, region offers an attractive route of administration for systemic drug delivery. The mucosa has a rich blood supply and it is relatively permeable.

Amongst the various routes of drug delivery, oral route is perhaps the most preferred to the patient and the clinician alike. However, per-oral administration of drugs has disadvantages such as hepatic first pass metabolism and enzymatic degradation within the gastro-intestinal tract, that prohibit oral administration of certain classes of drugs especially peptides and proteins.

Medical gases are pharmaceutical molecules which offer solutions to a wide array of medical needs. More specifically however, gases such as argon, helium, hydrogen, hydrogen sulfide, oxygen, ozone, xenon have recently come under increased exploration in the literature for their potential therapeutic uses in drug withdrawal suppressing effects and with various brain disease states including hypoxia-ischemia, cerebral hemorrhages, and traumatic brain injuries.

Volatile anesthetics have been extensively studied for decades with regard to their potential neuroprotective properties. A colorless, heavy, odorless noble gas, xenon has been of particular interest to researchers because of its possible neuroprotective properties. For example, Petzel and Kox (U.S. Pat. No. 8,143,317) describe the use of xenon for treating neurointoxications. Abraini et al. describe an inhalable gaseous medicament for treating neurointoxications (US2014120184) and for treating ischemic insults (WO2010035074). Still an inhalable aerosol medicament for the treatment or prevention of pain is described in US2002033174.

Argon is recognized to have a significant stabilizing effect on naloxone binding (also naltrexone). Inactivation of naloxone binding to rat brain membrane-bound mu-opioid receptors (Belokonova et al., Biokhimilia. 1993. 58 (12) 1945-1958).

Molecule related to mu-opioid receptors, such as argon, provides benefits to hyperactivity, attention deficit and autism (Rauhut et al., Pharmacol. Biochem Behav. 2002, 73: 611-622; and Aman M G and Langworthy. J. Autism Dev. Disord. 2000. 30: 451-459); sleep disorders (Vasquez-Palacios, 2004); eating and metabolic disorders (King et al., Biol. Psychiatry. 2013, 73: 924-930; and Kurbanov et al., J. Psychopharmacol. 2012, 26: 1244-1251).

Inert gas narcosis, such as argon, induces a decrease of the dopamine release at the striatum level, structure involved in the regulation of the extrapyramidal motricity (Balon et al., Life Sci. 72: 24, 2731-2740, 2003).

Results from in vitro and various animal models have consistently demonstrated organo-protective properties of xenon, mainly in settings of ischemia and reperfusion injury (Derwall et al., Minerva Anestesiol. 75. 37-45, 2009).

Nakao et al. (J Clin Biochem Nutr. January 2009; 44(1): 1-13.) provide an overview of some medicinal therapeutic gas and their use in treating various diseases (see Table 1).

Therapeutic gases have also been used for the treatment of ischemia and reperfusion (Holger K Eltzschig & Tobias Eckle, Nature Medicine 17, 1391-1401 (2011)).

It is clear from the literature that more gases are now being found new uses in therapies.

To date, to carry on these therapies, the volatile anesthetics or gases are administered through the airways by inhalation by the mouth and/or nose, using a mask connected by a gas bottle. Such therapies can currently only be administered at the hospital or in a clinic under supervision for greater control of the administration of the gases through the mask. Moreover, patients are generally not equipped to store gas bottles. Hence, a patient undergoing such gas therapy would need to go to a clinic or to the hospital for receiving the treatment.

Recently, some authors have suggested dissolving gases in water for ingestion as an alternate way to introduce gas in the system (Schoenfeld, 2012).

Further, Britton et al. have developed a pressurization-freeze method to encapsulate Xenon into echogenic liposomes (Xe-ELIP) and have modulated local gas release with transvascular ultrasound exposure (Britton, 2010).

Numerous patents such as U.S. Pat. No. 3,012,893 of Kremzner and Mitchell; U.S. Pat. Nos. 3,985,909 and 3,985,910 of Kirkpatrick and U.S. Pat. No. 4,001,457 of Hegadorn which are incorporated herein by reference, describe gasified candy containing a gas, such as carbon dioxide.

$CO_2$ has also been incorporated in candy or popping candy as apparent from Ahn and Lee (U.S. Pat. No. 5,439,698), Escola Gallart (U.S. Pat. No. 4,952,417) and Bayes Turull (U.S. Pat. No. 5,165,951).

Zeller et al. (U.S. Pat. No. 8,110,241) also describe a foaming soluble coffee powder containing pressurized gas for producing foam at the surface of the beverage.

Darbyshire et al. (U.S. Pat. No. 6,953,592), when faced with the problem of increasing the solubility of powders, have suggested a method of increasing the solubility or dispersibility of such powder using a gas.

Simonsen and Bach (US 20020081738) describe particles comprising a coating and a core particle comprising an active compound, such as an enzyme, wherein the coating comprises a gas component to reduce dust upon making such particles, for the safety of the workers, and to improve elasticity of the particles.

Despite the above, gases used in therapies are still now a day administered by inhalation, and still require the patient to get to a clinic or an hospital for receiving the treatment.

It would be highly desirable to be provided with a new delivery dose vehicle that would allow the patient to uptake its therapeutic gases much like any other compounds formulated in dose caplets or tablets.

SUMMARY

It is an object of the present invention to provide a novel oral dosage form for administration of therapeutic gases via the buccal mucosa of a subject.

It is a further object of the present invention to provide a novel mode of administration of gas therapy that allows the patient to self-administer such therapy.

According to an embodiment, there is provided a buccal delivery dosage form for buccal mucosal absorption of a therapeutic gas. In one embodiment, the buccal delivery dosage form comprises:
 a) at least one pressurized therapeutic gas;
 b) at least one crystallized excipient entrapping the gas.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
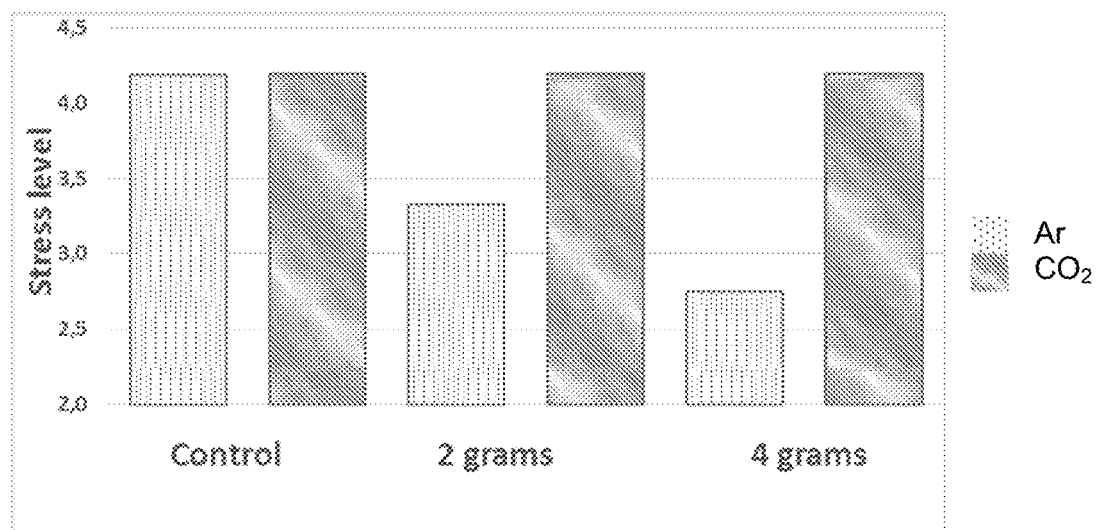
FIG. 1 is a graph illustrating the diminution of the relative stress level relative to buccal mucosa absorption of Argon or carbon dioxide entrapped in the delivery dosage form of the invention.

In one embodiment, there is disclosed a novel way to administer a therapeutic gas to be absorbed through the buccal mucosa, either sublingual, by the mucosa of the inside of the cheek or the mucosa of the gum.

According to one embodiment of the present invention, the dosage form of the present invention may further comprise an active ingredient, complementing or supplementing the effect of the therapeutic gas chosen for a given therapy.

The crystallized excipient may be for example a sugar, a polyol or a salt thereof, or any ingredient that crystallizes, allowing entrapping with the crystallized ingredient the therapeutic gas.

The sugar may be for example a commercially-available sugar employed in the confectionery industry. The crystallized excipient may then be a crystallized sugar or a mixture of crystallized sugars such as glucose, fructose, sucrose, lactose, corn syrup, glucose syrup, starch syrup, etc.

The polyol, also often referred to as a sugar-free substitute, may also be a commercially-available polyol employed in the confectionery industry. The polyol is preferably selected from the group consisting of isomalt, lactitol, maltitol, mannitol, sorbitol, xylitol, isosorbide, etc.

In one aspect, the pressurized gas to be entrapped within the crystallized excipient is preferably at least one selected from the group consisting of acetylene, argon, ethylene, helium, hydrogen, hydrogen sulfide, krypton, neon, nitrogen, nitric oxide, oxygen, ozone, sulfur dioxide, and xenon.

Preferably the therapeutic gas used in the present invention is Xenon.

Alternatively, still preferably, the therapeutic gas is Argon.

In a further preferred alternative, the therapeutic gas is a mixture of argon and xenon.

According to one embodiment of the present invention, the buccal delivery dosage form of the present invention comes in the shape of small bits of crystallized sugars (such as sucrose, lactose and glucose syrup) or crystallized polyols within which the therapeutic gas has been entrapped. According to the present invention, the buccal delivery dosage form is made by mixing ingredients including sugars and/or polyols as defined above, and heating until they melt, then exposing the mixture to the pressurized therapeutic gas and allowing the gaseous mixture to cool, thereby entrapping the therapeutic gas therein. The process causes tiny pressure bubbles to be trapped inside the crystallized excipient. According to one embodiment of the present invention, the buccal delivery dosage form is prepared without any additional ingredient. According to another embodiment of the present invention, the buccal delivery dosage form may also contain one or more additional active ingredients.

The fast liberation of the therapeutic gas upon solubilization of the crystallized excipient permits the absorption of the gas through the buccal mucosa, via the trans- and/or paracellular routes.

According to a preferred embodiment of the present invention, the buccal delivery dosage form preferably contains a crystallised polyol like isomalt.

The expression "buccal delivery dosage form" as used herein is intended to mean a vehicle or carrier for administration of a therapeutic gas in the mouth of a subject with absorption through the buccal mucosa, by-passing of gastrointestinal tract and the airways. Such dosage forms include pill, tablet, gum, micro-tablet, micro-spheres (e.g. with diameters of about 1 µm to about 1 mm), nano-spheres (e.g. with diameters of about 100 nm, microsomes (about 1 µm to about 1 mm), gel, colloid, colloidosome, nano-capsule (e.g. with diameters of about 1 µm), pastille, paste, chewing gum, crystals, liquid, caplet or capsule, all to be dissolved in the mouth of the patient for releasing therein the entrapped therapeutic gas.

The expression "buccal mucosa" as used herein is intended to include the mucosa around and underneath the tongue (sublingual), the inner side of the cheeks, and the gum and hard palate.

The expression "crystallized excipient" as used herein is intended to refer to the sugar or polyol that has been heated, melted and then cooled down. If a gas has been injected into the sugar or polyol when heated, melted and cooled down, then the crystallized excipient also contain a pressurized gas therein. If no gas is being injected upon heating, melting and cooling down of the sugar or polyol, then the resultant is only a crystallized sugar or polyol. The sugar and polyol, as any excipient is inert with respect to the therapeutic gas, i.e. does not react with the gas upon injection and crystallization.

The expression "therapeutic gas" as used herein is intended to refer to a gas known for its therapeutic effect, or a gas for which a demonstration of its therapeutic effect has been previously demonstrated.

The term "subject" is intended to mean any mammals, including without limitation, human, equine, bovine, caprine, feline, canine, ovine, rodents, etc.

Additional Active Ingredients

The buccal delivery dosage form may further comprise one or more additional active ingredients. The additional active ingredients may be a plant extract, a natural compound or a pharmaceutical drug. It is understood that the additional active ingredient may have a known biological effect, complementing or supplementing the effect of the therapeutic gas chosen for a given therapy.

The expression "additional active ingredient" is intended to mean any pharmaceutically, pharmacologically, or biologically active substance such as, for example, a pharmaceutical drug, or a vitamin that is biologically active. These include without limitations enzyme inhibitors (e.g. carbonic anhydrase inhibitors), ion channel blockers (e.g. calcium channel blockers), antacids, amino acid, reflux suppressant, antiflatulents, antidopaminergics, proton pump inhibitors, $H_2$-receptor antagonists, cytoprotectants, prostaglandin and prostaglandin analogues, laxatives, antispasmodics, antidiarrheals, bile acid sequestrants, opioids, beta-receptor blocker, diuretics, cardiac glycosides, antiarrhytmics, nitrate, antiangials, vasoconstrictor, vasodilators, peripheral activators, ACE inhibitors, angiotensin receptor blockers, alpha-blocker, anticoagulants, heparin, antiplatelet drugs fibrinolytics, anti-hemophilic factors, haemostatic drugs, hypolipidaemic agents, statins, hyphotics, anaesthetics, antipsychotics, antidepressants (such as tricyclic antidepressant, monoamine oxidase B inhibitors, lithium salts and selective serotonin reuptake inhibitors), antiemetics, anticonvulsants/antiepileptics, anxiolytics, barbiturates, folic acid, phenolic compounds, movement disorder drugs, fatty acids (such as oleic acid, linoleic acid, myristoleic acid, palmitoleic acid, sapienic acid, α-linolenic acid or omega-3, arachidonic acid, eicosapentaenoic acid, erucic acid, docosahexaenoic acid, lauric acid, myristic acid, palmitic acid, stearic acid, arachidic acid, stimulants, benzodiazepine, cyclopyrrolones, dopamine agonists/antagonists, antihistamines, bromide, scopolamine, cholinergics, anticholinergics, emetics, cannabinoids, 5-HT antagonists, NSAIDs (such as COX-2 selective inhibitors), opioids, orphans drugs (such as paracetamol), muscle relaxant, neuromuscular drugs, anticholinesterases, adrenergic blockers, antibiotics, am inoglycosides, sulfa drugs, fluoroquinolones, antiviral drugs, anti-fungal, corticosteroids, mast cell inhibitors, prostaglandin agonists/inhibitors, steroids, antiseptics, anesthetics, androgens, antiandrogens, gonadotropin, human growth factor, insulin, antidiabetics, thyroid hormones, antityroid drugs, calcitonin, diphosponate, vasopressin analogues, quinolones, 5-alpha reductase inhibitor, selective alpha-blockers, sildenafils, tadalafils, fertility drugs, hormonal contraception, ormeloxifene, antifibrinolytics, follicle stimulating hormone, luteinising hormone, gamolenic acid, gonadotropin release inhibitor, progestin, oestrogen, gonadorelin, clomiphene, tamoxifen, diethyl stilbestrol, antileprotics, antituberculous drugs, antimalarials, anthelmintics, amoebicides, antivirals, antiprotozoals, vaccines, immunoglobulins, immunosuppressants, interferons, monoclonal antibodies, anti-allergics, cytotoxic drugs, therapeutic antibodies, somatostatin inhibitors, recombinant interleukins, G-CSF, erythropoietin, vitamins, pigments, antioxidant, laxative, mineral supplements (such as calcium, chromium, folate, iron, magnesium, selenium, nitrate . . . ), natural compounds, including without limitations bilobalide, ginkgolide, hypericine, hyperforin, silymarine, silibinin, a lignan, diosgenine, curcumin, hydroxycitric acid, eleutherocide B, eleutherocide E, a phytosterol, a saponin, sarsapic acid, yohimbine, gingerol, phytosterols including without limitations diosgenine, brassicasterol, cam paestrol, 5α-cholestane, β-sitosterone, β-sitosterol, stigmasterol, etc.

If the additional active ingredient is a plant extract, such plant extract may be chosen for example, without limitation, from Absinthe (*Artemisia absinthum*), Alfalfa (*Medicago sativa*), Aloe (*Aloe barbadensis*), Angelica (*Angelica archangelica* and *sinensis*), Anise (*Pimpinella anisum*), Arnica (*Arnica montana*), Ashwaganda (*Withania somnifera*), Astragalus (*Astragalus membranaceus*), Betony (*Stachys/Betonica officinalis*), Bilberry/Huckleberry (*Vaccinium* spp.), Bitter melon fruit (*Momordica charantia*), Black cohash (*Cimicifuga racemosa*), Bladderwrack (*Fucus versiculosus*), Blessed thistle (*Cnicus benedictus*), Blue cohosh (*Caulophyllum thalictroides*), Boneset (*Eupatorium perforatum*), Burdock (*Arctium lappa*), *Caesalpinia benthamiana*, Calendula (*Calendula officinalis*), California poppy (*Eschscholzia californica*), Caraway (*Carum carvi*), Cardamom (*Elettaria cardamomum*), Cascara (*Rhamnus purshiana*), Catnip (*Nepeta cataria*), Cayenne (*Capsicum frutescens*), Cedar, Western (*Thuja plicata* or *occidentalis*), Chamomile (*Matricaria recutita*), Chaparral (*Larrea mexicana*), Chaste tree berry (*Vitex agnus castus*), Chickweed (*Stellaria media*), Cinnamon (*Cinnamomum* spp.), Cleavers (*Galium aparine*), Coltsfoot (*Tussilago farfara*), Comfrey (*Symphytum officinalis*), Corn silk (*Zea mays*), Corynanthe yohimbe, Cramp bark (*Viburnum opulus*), Dandelion (*Taraxacum officinalis*), Devil's club (*Oplopanax horridus*), *Dioscorea villosa*, Dong quai (*Angelica sinensis*), Echinacea (*Echinacea* spp.), Elder flowers (*Sambucus* spp.), Elecampane (*Inula helenium*), Eyebright (*Euphrasia officinalis*), *Fadogia agrestis*, Fennel (*Foeniculum vulgare*), Fenugreek (*Trigonella foenum-graecum*), Feverfew (*Tanacetum parthenium*), Flax seed (*Linum usitatissimum*), Garcinia Cambogia, Garlic (*Allium sativa*), Geranium (*Geranium maculatum*), Ginger (*Zingiber officinalis*), Ginkgo (*Ginkgo biloba*), Ginseng (*Panax* spp.), Goldenrod (*Solidago* spp.), Goldenseal (*Hydrastis canadensis*), Gotu kola (*Centella asiatica*), Gravel root (*Eupatorium purpureum*), Hawthorne (*Crataegus* spp.), Hibiscus subdariffa, Hops (*Humulus lupulus*), Horehound (*Marrubium vulgaris*), Horsetail (*Equisetum arvense*), *Hippophae rhamnoides*, Hyssop (*Hyssopus officinalis*), Kava kava (*Piper methysticum*), Lady's mantle (*Alchemilla vulgaris*), Lemon balm (*Melissa officinalis*), *Lepidium meyenii*, Licorice (*Glycyrrhiza glabra*), Linden flower (*Tilia* spp.), Lobelia (*Lobelia inflata*), Lomatium (*Lomatium dissectum*), Lungwort (*Sticta pulmonaria*), Marshmallow (*Althea officinalis*), *Massularia acuminate*, Meadowsweet (*Filipendula ulmaria*), *Microdesmis keayana*, Milk thistle (*Silybum marianum*), *Morinda citrifolia*, Motherwort (*Leonurus cardiaca*), Mucuna pruriens, Mugwort (*Artemisia vulgaris*), Mullein (*Verbascum thapsus*), Myrrh gum (*Commiphora myrrha*), Nettle (*Urtica* spp.), Noni (*Morinda citrifolia*), Nopal (*Opuntia ficus indica*), Oat (*Avena sativa*), *Oenothera biennis*, Old man's beard, Usnea (*Usnea* spp.), Oregon grape root and barberry (*Mahonia* spp.), Osha (*Ligusticum porteri*), Parsley (*Petroselinum crispum*), Passionflower (*Passiflora incarnata*), Peppermint (*Mentha piperita*), Plantain (*Plantago* spp.), Poplar buds (*Populus* spp.), Red clover (*Trifolium pratense*), Red raspberry (*Rubus idaeus*), Red root (*Ceanothus americanus*), *Rhodiola Rosea*, Rosemary (*Rosmarinus officinalis*), Sage (*Salvia officinalis*), Saint John's wort (*Hypericum perforatum*), Saw palmetto (*Serenoa repens*), Sea-buckthorn (*Hippophae rhamnoides*), Sesame seed (*Sesamum indicum*), Siberian ginseng (*Eleutherococcus senticosus*), Skullcap (*Scutellaria laterifolia*), Slippery elm (*Ulmus* spp. (*rubra, fulva*)), Thyme (*Thymus vulgaris*), *Triblus terrestris*, Tumeric (*Curcuma longa*), *Thuya occidentalis*, Uva ursi (*Arctostaphylos uva ursi*), Valerian (*Valeriana officinalis*), Vervain (*Verbena officinalis*), White oak bark (*Quercus alba*), Wild cherry (*Prunus* spp.), Willow (*Salix* spp.), Yarrow (*Achillea millefolium*), Yellow dock (*Rumex crispus/ obtusifolius*), or combinations thereof.

If the addition active ingredient is a natural compound, such natural compound may also be, for example, without limitations, Astaxanthin, Bilobalide, Biotine, Catechine, Choline, Coenzyme $Q_{10}$, Conjugated, Curcumine, Lecithin, linoleic acid, Ginkgolide, Glucosamine, Hypericine, Hyperforin, Silymarine, Silibinin, a Lignan, Diosgenine, hydroxycitric acid, eleutherocide B, Eleutherocide E, L-carnitine, Leucine, Megastigmane glycoside, Melatonine, Niacinamide, Niacine, Omega-3, Pantothenic acid, a phytosterol, Phospholipids, Pinolenic acid, Resveratrol, Riboflavine, Rosiglitazone, Serotonin, Theobromine, Theophylline, Thiamine, g-aminobutyric acid (pathway), a saponin, sarsapic acid, Vitamin $B_{12}$, Yohimbine, gingerol, or combinations thereof.

Uses and Methods

According to another embodiment of the present invention there is provided a therapeutic method as described herein comprising administering a therapeutically effective amount of a buccal delivery dosage form according to the present invention, where the therapeutic gas is absorbed through the buccal mucosa and produces the therapeutic effect anticipated.

According to another embodiment of the present invention, there is provided the use of the buccal delivery dosage form for administering a therapeutic gas through the buccal mucosa of a patient.

The methods and uses of therapeutic gas include improving oxidative stress-mediated diseases including neonatal cerebral hypoxia; Parkinson's disease; ischemia/reperfusion of spinal cord, heart, lung, liver, kidney, and intestine; transplantation of lung, heart, kidney, and intestine; hemodialysis, inflammatory and mitochondrial myopathies, brain stem infarction, and radiation-induced adverse effects. Cortical neuroprotection (excitoxic, ischemic insult, traumatic brain injury, avoiding increasing subcortical brain damage), anesthetic, stroke, hypoxia, neurocognitive dysfunction, chronic lung diseases, cardiopulmonary disease, infected wounds, circulatory disorders, viral diseases, cancer, rheumatism/arthritis, ginvival and periodontal diseases, antimicrobial, inflammation, hypertension, cataract, aging, pulmonary hypertension.

The present invention will be more readily understood by referring to the following examples which are given to illustrate the invention rather than to limit its scope. By way of the following examples, it is being shown hereinafter that therapeutic gases can be entrapped within a crystallized excipient, with one simple mode of preparation of the buccal delivery dosage form of the invention. It is also shown that entrapped therapeutic gases can indeed be absorbed through the buccal mucosa and have a therapeutic effect. This now opens the way for a whole new mode of administration of therapeutic gases, simplifying any treatment involving the use of such therapeutic gases.

Example 1

Preparation of the Buccal Delivery Dosage Form

A buccal delivery dosage form is prepared by heating the excipient, the isomalt, to a temperature of about 330-338° C. for the isomalt to melt and turn liquid. Then inject into the mixture under agitation pressurized Argon, the therapeutic gas, about 600 pounds per square inch; or approx. 41.37 Bar and allow the isomalt/gas mixture to cool down, whereby Argon is entrapped with the re-crystallized isomalt. The process causes tiny high pressure bubbles to be trapped inside the re-crystallized isomalt. The dosage form is then broken down and sieved to the desired size (from 1 to 5 mm), and bagged into 2 grams doses.

Example II

Absorbed Argon for Reducing Stress/Anxiety

Bags of 2 grams of the Argon-containing buccal delivery dosage form as prepared in Example 1 were handed out to volunteers for testing. The cohort consisted of 8 healthy volunteers between the age of 15 and 60 years old. To better access the effect and absorption of Argon, the experiment was repeated on the same volunteers with a buccal delivery dosage form containing carbon dioxide only.

Protocol:
  Before any uptake, each volunteer was asked to evaluate is stress level on a scale from 1 to 10 (1 is near a meditative state and 10 is the maximum stress and anxiety). This value is the control value.
  Then 2 g was taken orally (avoiding swallowing); waft 5 minutes after complete melting and re-evaluation the level of stress/anxiety.
  After 5 minutes, take a second 2 g of the buccal delivery dosage form and re-evaluate the level of stress/anxiety.
  The volunteers repeated the protocol 3 times on different days for the $CO_2$-containing dosage form and the Argon-containing dosage form.

A questionnaire was given to the volunteers to assist them in evaluating their stress/anxiety level. Amongst other criteria, the volunteers we asked to note the level of stress in normal conditions, their heart rate pulse, and any other effects such as any tickling feeling or any other feelings of the lips, tongue or inner side of the cheeks. The volunteers noted a feeling of calmness and relaxation after having taken even a single dose of 2 grams. The criteria were marked before taking the dosage form and re-evaluated after 5 minutes.

After the buccal absorption of 2 g of Argon-containing crystal, the stress/anxiety level of volunteers decrease of 0.9 (21%) and 1.4 (34%) after the absorption of 4 g of crystal (see FIG. 1). These results mean that the Argon was released and absorbed by the buccal mucosa into the body of the volunteers. The absorption of 2 to 4 g of trapped Argon in crystallized isomalt, did reduce significantly the stress/anxiety level. Based on the literature, the results can be extrapolated to hyperactivity and attention deficit. It is clear from FIG. 1 that this reduction of anxiety is the result of the Argon gas, when considering the effect of the same product filled with $CO_2$, which did not cause any reduction at all.

Example III

Effect of Absorbed Argon or $CO_2$ on the Heart Beat Rate

The same protocol as used in Example II was used in this example. The heart beat rate was measured after 2 g and after 4 g of the buccal delivery dosage form (representing about 2.76 and 5.52 ml of gas, respectively) as prepared in Example 1 was orally taken.

Each volunteer repeated the protocol 3 times on different days for each one of the $CO_2$-containing dosage form and the Argon-containing dosage form.

Figure 2:
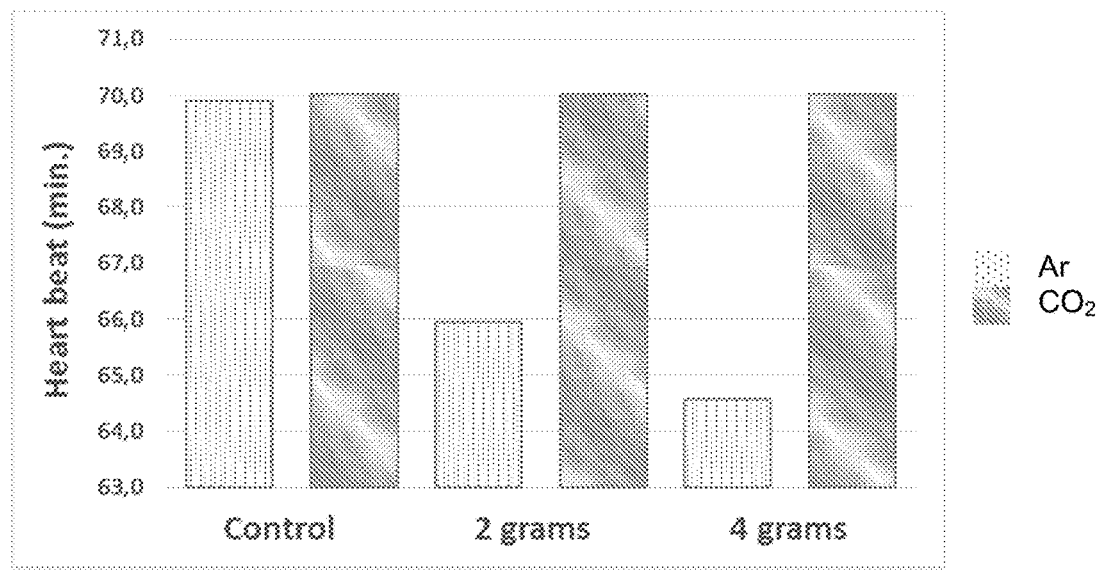
FIG. 2 is a graph illustrating the diminution of the heart beat rate relative to buccal mucosa absorption of Argon or carbon dioxide entrapped in the delivery dosage form of the invention.

These results as illustrated in FIG. 2 show that the Argon was released and absorbed through the buccal mucosa into the body of the volunteers. The absorption of 2 to 4 g of trapped Argon in a crystallized isomalt did reduce significantly the heart beat rate by 3-6 bpm in average (4-8%, see FIG. 2). It is worthy to note that the $CO_2$-containing dosage form did not cause a reduction of the heart beat rate. In fact, the effect of the $CO_2$ is about equal to the effect of the control, as if no gas was being administered. This even more strongly confirm that the effect of the reduction on the heart beat rate is indeed due to the absorption of Argon.

Example IV

Volume of Gas Entrapped in the Crystals

The volume of gas entrapped in the crystals of the buccal delivery dosage form of the invention was measured in relation to a volume of water displaced. This experiment was conducted at normal pressure and temperature, i.e. 1 atm and about 22° C. The volume of water displaced equals to the volume of gas released by the crystals. Briefly, Argon-entrapping crystals as prepared above were sieved to obtain 3 sizes of crystals, namely crystals either smaller than 2 mm (group 1), either between 2-4 mm (group 2) or larger than 4 mm (group 3) in size. Then for each group, the follow set-up was used: an inverted 50 ml graduated cylinder was inserted over and above the neck of a 100 ml flask, and both the flask and the cylinder were filled with water in a water reservoir. Then, when the gas is released from the crystals that are being dissolved in the flask, the gas so released tends to rise above the water, rising into the cylinder, chasing out water from the cylinder. In practice, 10 grams of crystals were inserted into the 100 ml flask. The flask is then filled with water and submerged into the reservoir. Finally, the 50 ml graduated cylinder is filled with water and inverted on top and above the neck of the flask, in fluid continuity with the flask. Upon solubilization of the crystals, Argon was being released, causing an accumulation of Argon into the graduated cylinder. Then a final measure of the volume of gas in the graduated cylinder was made.

Figure 3:
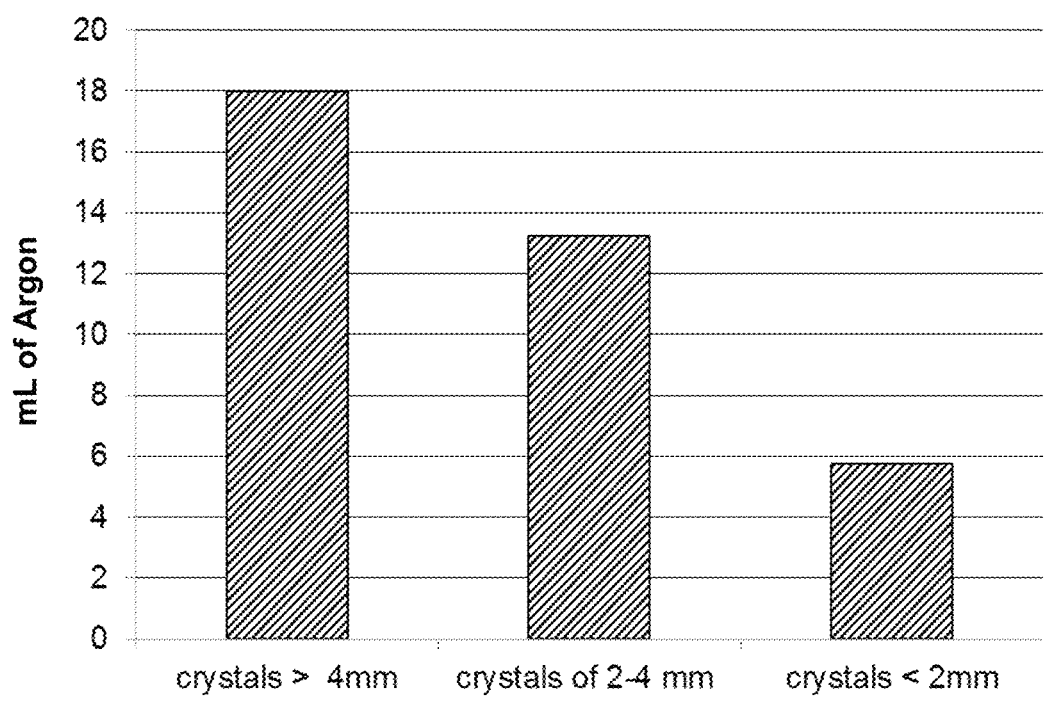
FIG. 3 is a graph illustrating the volume of Argon entrapped in the delivery dosage form of the invention as a function of the size of the crystals of the delivery dosage form.

The results of the Argon measured are illustrated in FIG. 3 and in Table 1 below.

TABLE 1

Volume of gas entrapped in the crystals

| Size | Volume of gas (ml or cc) |
|---|---|
| group 1 (<2 mm) | 5.8 |
| group 2 (2-4 mm) | 13.3 |
| group 3 (>4 mm) | 18.0 |

As can be seen from FIG. 3, the result obtain is directly linear with the size of the crystals. In average, all three groups pooled together, there is in average about 13.8 cc (or ml) of therapeutic gas in 10 grams of crystals.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for administering a therapeutic gas to a patient in need thereof, said method comprising administering in the mouth of said patient in need of such therapeutic gas a buccal delivery dosage form comprising:
    a) at least one crystallized excipient; and
    b) at least one therapeutic gas entrapped within the crystallized excipient,
    wherein said buccal delivery dosage form releases the therapeutic gas entrapped therein upon solubilization of said crystallized excipient in contact with the saliva in the mouth of the patient, said gas being absorbed through the buccal mucosa, and wherein said buccal delivery dosage form does not contain any additional active ingredient.

2. The method of claim 1, wherein the crystallized excipient is a sugar or a polyol.

3. The method of claim 2, wherein the sugar is a sugar commercially available in the confectionary industry.

4. The method of claim 2, wherein the sugar is selected from the group consisting of glucose, fructose, sucrose, lactose, corn syrup, starch syrup, and glucose syrup.

5. The method of claim 2, wherein the polyol is a polyol commercially available in the confectionary industry.

6. The method of claim 2, wherein the polyol is selected from the group consisting of isomalt, lactitol, maltitol, mannitol, sorbitol, xylitol, and isosorbide.

7. The method of claim 1, wherein the therapeutic gas is a noble gas.

8. The method of claim 1, wherein the therapeutic gas is selected from the group consisting of acetylene, argon, ethylene, helium, hydrogen, hydrogen sulfide, krypton, neon, nitrogen, nitric oxide, oxygen, ozone, sulfur dioxide, and xenon.

9. The method of claim 1, wherein the crystallized excipient contains about 1.3 to about 1.38 ml of therapeutic gas entrapped therein.

10. A method for reducing stress and/or anxiety, said method comprising the step of administering in the in the mouth of a patient in need of such treatment a buccal delivery dosage form comprising:
    a) at least one crystallized excipient; and
    b) argon gas entrapped within the crystallized excipient,
    wherein said buccal delivery dosage form releases the argon gas entrapped therein upon solubilization of said crystallized excipient in contact with the saliva in the mouth of the patient, said argon gas being absorbed through the buccal mucosa for relieving stress and/or anxiety.

11. The method of claim 10, wherein the crystallized excipient contains about 1.3 to about 1.38 ml of argon gas entrapped therein.

* * * * *